(12) United States Patent
Stone (10) Patent No.: US 7,217,246 B1
(45) Date of Patent: May 15, 2007

(54) METHOD AND APPARATUS FOR RETAINING A FIXATION PIN TO A CANNULA

(75) Inventor: Kevin T Stone, Winona Lake, IN (US)

(73) Assignee: Biomet Sports Medicine, Inc., Warsaw, IN (US)

( * ) Notice: Subject to any disclaimer, the term of this patent is extended or adjusted under 35 U.S.C. 154(b) by 172 days.

(21) Appl. No.: 10/870,873

(22) Filed: Jun. 17, 2004

(51) Int. Cl.
*A61B 5/00* (2006.01)
*A61M 25/00* (2006.01)

(52) U.S. Cl. ...................................... 600/585
(58) Field of Classification Search ................ 600/585; 604/523, 524, 526, 528, 23, 30, 103, 117, 604/158, 175, 236, 247, 264, 533, 102.01, 604/167.06, 96.01, 165.02, 164.03, 103.04; 156/175, 173, 86, 294; 606/191, 194; 138/118
See application file for complete search history.

(56) References Cited

U.S. PATENT DOCUMENTS

| 4,946,443 | A | | 8/1990 | Hauser et al. |
|---|---|---|---|---|
| 5,267,958 | A | | 12/1993 | Buchbinder et al. |
| 5,357,978 | A | | 10/1994 | Turk |
| 5,746,720 | A | * | 5/1998 | Stouder, Jr. .................. 604/117 |
| 5,879,499 | A | * | 3/1999 | Corvi .......................... 156/175 |
| 6,007,522 | A | | 12/1999 | Agro et al. |
| 6,056,722 | A | * | 5/2000 | Jayaraman .............. 604/102.01 |
| 6,095,990 | A | | 8/2000 | Parodi |
| 6,096,009 | A | | 8/2000 | Windheuser et al. |
| 6,312,406 | B1 | | 11/2001 | Jayaraman |
| 6,346,093 | B1 | * | 2/2002 | Allman et al. .......... 604/167.06 |
| 6,520,951 | B1 | | 2/2003 | Carrillo, Jr. et al. |
| 6,746,442 | B2 | * | 6/2004 | Agro et al. .................. 604/523 |
| 6,926,707 | B2 | * | 8/2005 | Nash et al. .................. 604/533 |
| 2002/0029014 | A1 | | 3/2002 | Jayaraman |
| 2003/0018340 | A1 | | 1/2003 | Branch |
| 2003/0120208 | A1 | * | 6/2003 | Houser et al. ......... 604/103.04 |
| 2005/0165366 | A1 | * | 7/2005 | Brustad et al. ............. 604/264 |

* cited by examiner

*Primary Examiner*—Max F. Hindenburg
*Assistant Examiner*—Brian Szmal
(74) *Attorney, Agent, or Firm*—Harness, Dickey & Pierce, P.L.C.

(57) ABSTRACT

A medical device for placement in an incision. The medical device includes a cannula member configured to be inserted into the incision. The medical device also includes a guide wire holding member having a base member connected to the cannula member. Wall members are connected to said base member and form an open channel along said cannula member. A guide wire or fixation pin can be inserted into the guide wire holding member. The guide wire holding member can be configured as an open c-shaped channel or a plurality of curled tabs to hold the guide wire. The various configurations of the guide wire holding member can be constructed without the use of tapered or flared pins in an injection molding manufacturing process.

8 Claims, 7 Drawing Sheets

METHOD AND APPARATUS FOR RETAINING A FIXATION PIN TO A CANNULA

FIELD

The present invention relates to a medical device and more particularly relates to a cannula with improved guide wire holding members.

BACKGROUND

Figures 1, 2, 3:
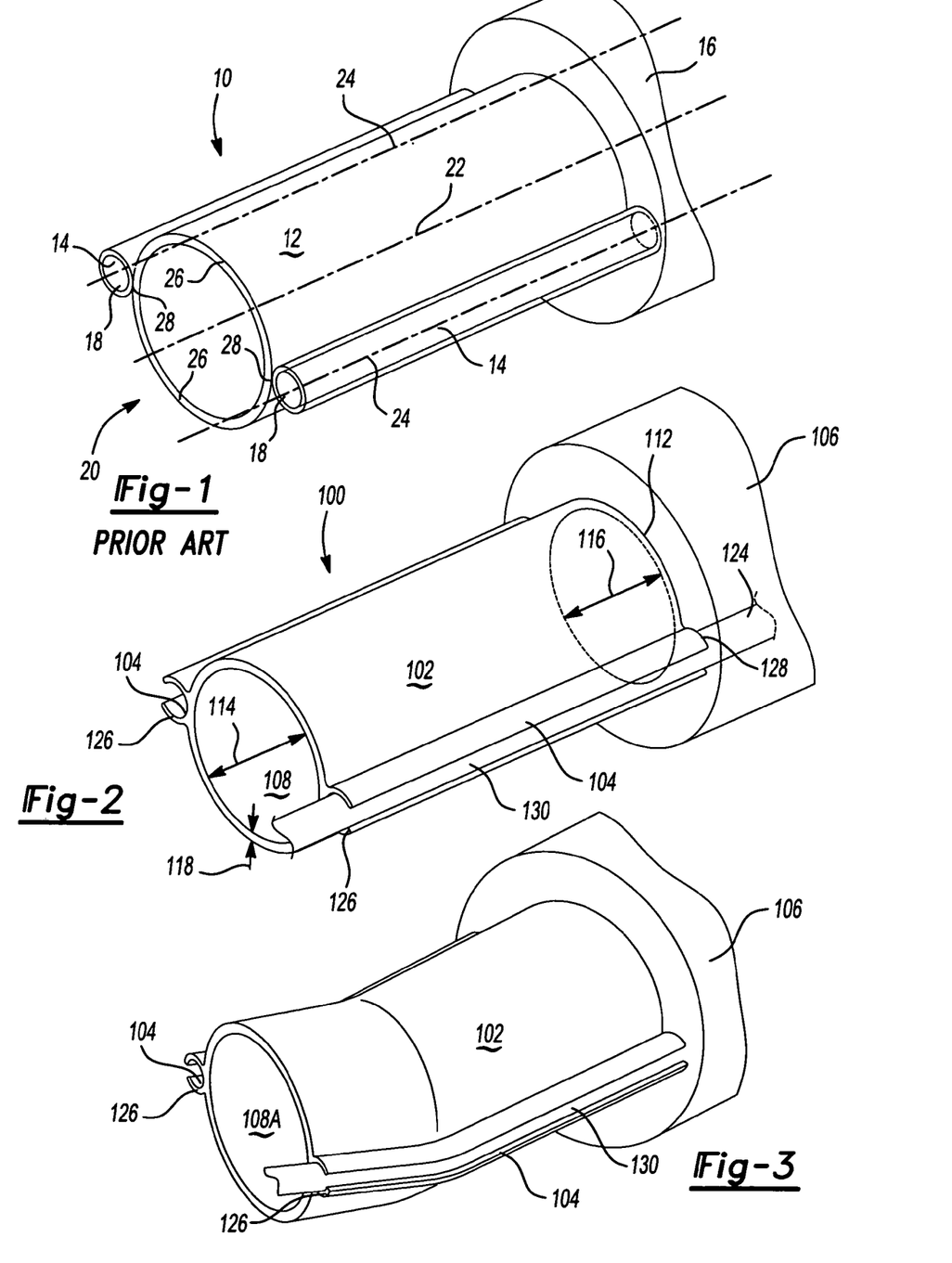
FIG. 1 is a perspective view of a conventional three-tube cannula having a larger tube and a pair of smaller tubes attached thereto.
FIG. 2 is a perspective view of a medical device of the present invention showing a cannula member and guide wire holding members connected thereto constructed in accordance with the teachings of the various embodiments of the present invention.
FIG. 3 is similar to FIG. 2 but shows a guide wire in one of the guide wire holding members steering a portion of the cannula member.

With specific reference to FIG. 1, a conventional three-tube cannula is shown and generally indicated by reference numeral 10. The three-tube cannula 10 includes a larger tube 12 to which a pair of smaller tubes 14 are attached. An accessory end 16 is connected to the larger tube 12 and the pair of smaller tubes 14. Guide wires or fixation pins (not shown) can be inserted into a pair of openings 18 and threaded through the pair of smaller tubes 14, so that the three-tube cannula 10 can be supported on the guide wires or the fixation pins. The tip of the three-tube cannula 10 is generally indicated by reference number 20 and is configured to be inserted into a patient through an incision (not shown).

The three-tube cannula 10 is typically made in an injection molding machine (not shown). It will be appreciated that during the forming process the larger tube 12 and the pair of smaller tubes 14 may be formed over tapered pins (not shown but known to one skilled in the art) to ensure the length, diameter and wall thickness of each of the tubes 12, 14. Another consideration is the relative alignment of the larger tube 12 and the pair of smaller tubes 14. More specifically, the larger tube 12 is defined by a center line 22 and the pair of smaller tubes 14 is defined by associated center lines 24. It will be appreciated that as the length of the pins in a typical injection molding machine increase in length, the ability to produce the larger tube 12 in parallel alignment to the pair of smaller tubes 14 becomes more difficult and expensive.

As with any manufacturing process, exact parallel alignment is not always required or attainable. With that said, deviations from absolutely parallel may cause the wall thickness of either the larger tube 12 or the pair of smaller tubes 14 to be too thin when compared to the same cannula manufactured with correct alignment. If a wall thickness 26 is too thin, quality issues arise and the rejection rate from the injection molding machine may become unacceptably high. Moreover, a thickness at a junction indicated by reference numeral 28 between the larger tube 12 and the pair of smaller tubes 14 must not be too thin as the possibility exists of poking the guide wire through one of the smaller tubes 14 into the larger tube 12.

One technique in forming the pair of smaller tubes 14 and/or the primary tube 12 over the pins in the injection molding machine requires gradually flaring one end of the pins, to make it possible to remove the three-tube cannula 10 from the injection molding machine. Flaring is defined as a slight gradual increase of the diameter of a pin at one end when compared to the other end. Because the pins of the injection molding machine are flared or tapered, it necessarily means that one end of the smaller tubes 14 and/or the larger tube 12 will have a larger diameter when compared to an opposite end. This change in diameter necessarily means that the guide wires or fixation pins inserted into the smaller tubes 14 will not be constrained as well when compared to one of the smaller tubes 14 having a constant diameter throughout.

It is desirable to construct a three-tube cannula 10 without relying on pins when using an injection molding manufacturing process. It is also desirable to construct a three-tube cannula 10 that is easier to remove from the mold when compared to an injection molding design that relies on the pins. It is further desirable to construct a medical device that includes guide wire holding members that connect to a guide wire to provide sufficient stability during a medical procedure.

SUMMARY

A medical device for placement in an incision. The medical device includes a cannula member configured to be inserted into the incision. The medical device also includes a guide wire holding member having a base member connected to the cannula member. Wall members are connected to said base member and form an open channel along said cannula member. A guide wire or fixation pin can be inserted into the guide wire holding member. The guide wire holding member can be configured as an open c-shaped channel or a plurality of curled tabs to hold the guide wire.

Further areas of applicability of the present invention will become apparent from the appended claims and detailed description provided hereinafter. It should be understood that the specific examples in the detailed description, while indicating the various embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE VARIOUS EMBODIMENTS

The following description of the various embodiments is merely exemplary in nature and is in no way intended to limit the invention, its application, or uses.

With reference to FIG. 2, a medical device is generally indicated by reference numeral 100. The medical device 100 includes a main cannula 102 and at least one guide wire holding member 104 attached thereto. It will be appreciated that guide wire holding member 104 can be attached to the main cannula such that the guide wire holding member 104 is connected to the main cannula 102 and affixed with fasteners, bonding chemicals, or other suitable connecting members. The guide wire holder 104 can also be attached to the main cannula 102, such that the guide wire holder 104 is integral to the main cannula 102 and formed of one piece of material. As such, attached or connected thereto is defined as and refers to a one-piece integral construction or a multiple-piece construction attached with suitable fastener members.

Figures 11, 12:
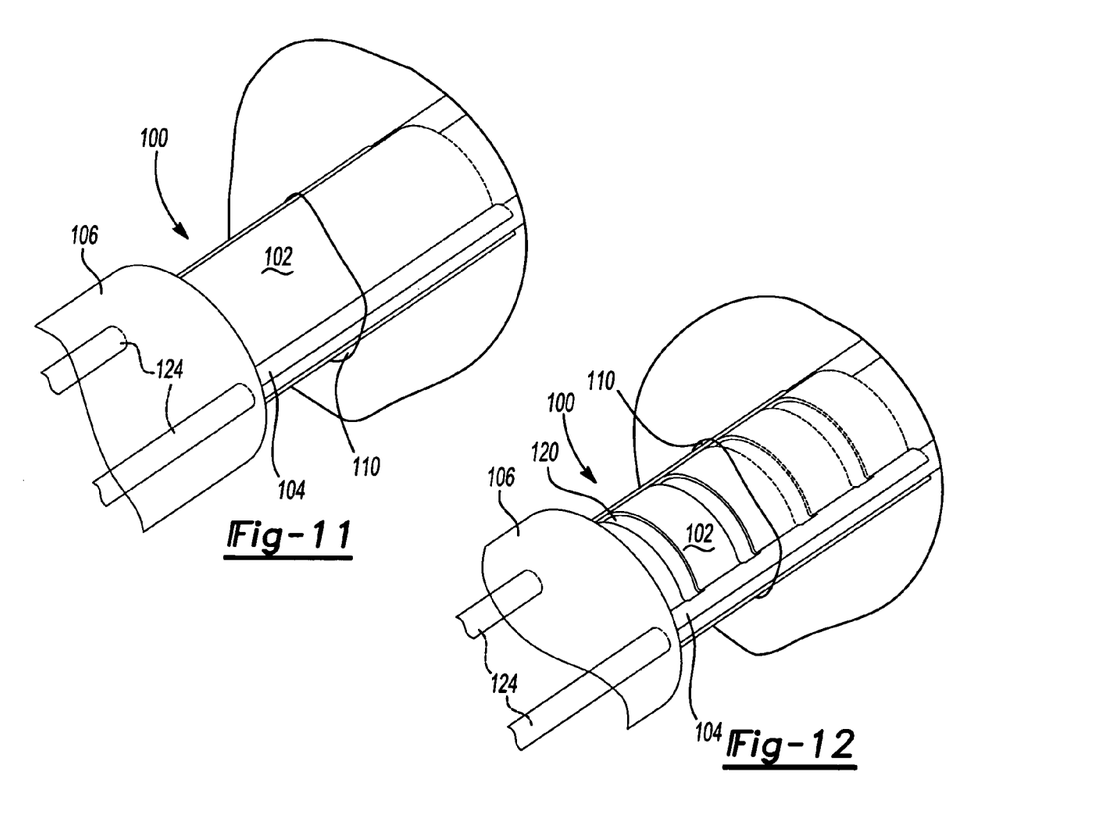
FIG. 11 is a partial perspective view of the medical device of FIG. 2 partially inserted into an incision and placed over a pair of guide wires.
FIG. 12 is a partial perspective view of the medical device of FIG. 5 partially inserted into the incision and placed over a pair of guide wires.
Figure 13:
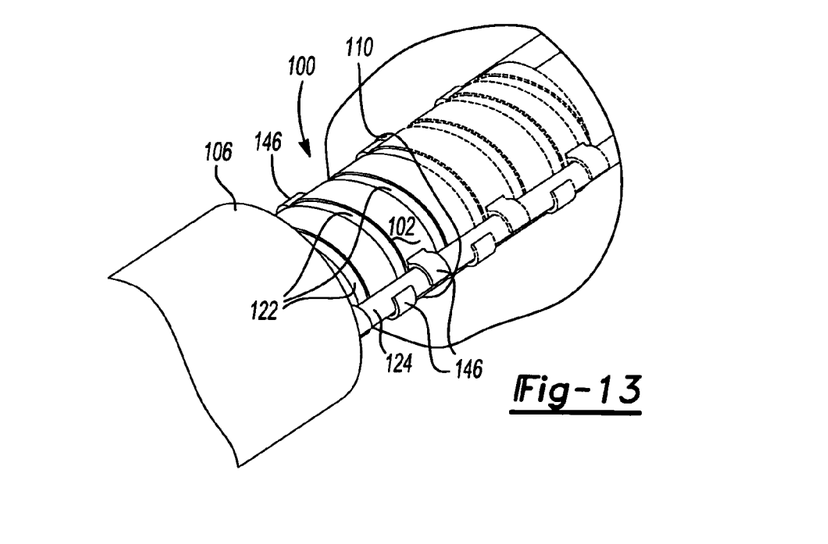
FIG. 13 is a partial perspective view of the medical device of FIG. 7 partially inserted into the incision and placed over a pair of guide wires.
Figure 14:
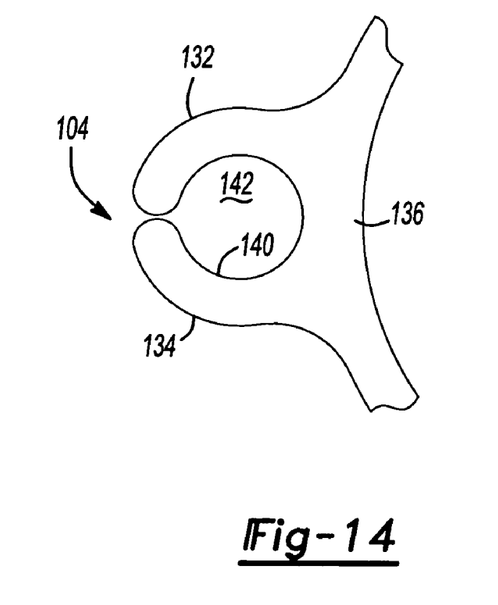
FIG. 14 is a partial front view of the guide wire holding member of FIG. 10 configured as an almost complete circle.

An optional accessory portion 106 is attached to the main cannula 102 and the guide wire holding member 104. The main cannula 102 is configured such that various medical devices (not shown) can be passed from the accessory portion 106 through the main cannula 102. A tip 108 of the main cannula 102 is configured to be inserted into a patient (not shown) through an incision 110, as depicted in FIGS. 11, 12 and 13. Various items can be passed from the accessory portion 106 through the main cannula 102 and into the patient. It will be appreciated that the various items can include but are not limited to balloon catheters, arthroscopic scopes, suction devices, or any other suitable tools to be inserted into a patient during a medical procedure.

The main cannula includes the tip 108 which is distal from a main cannula 112 connecting point that connects to the accessory portion 106. It will be appreciated that the main cannula 102 can be circular as depicted in FIG. 2, or can be configured with other shapes such as ovals or rectangular shapes as needed in various medical applications. The main cannula 102 has a tip diameter 114 and a connecting point diameter 116 both of which can be identical or vary from one another. More specifically, the connecting point diameter 116 can be smaller than the tip diameter 114 when the medical device 100 can be configured to suspend a balloon catheter (not shown) in the main cannula 102 and hold the balloon catheter within the accessory portion 106. Moreover, the length and the diameter of the main cannula 102 can be varied based on the medical application as needed.

Figure 9:
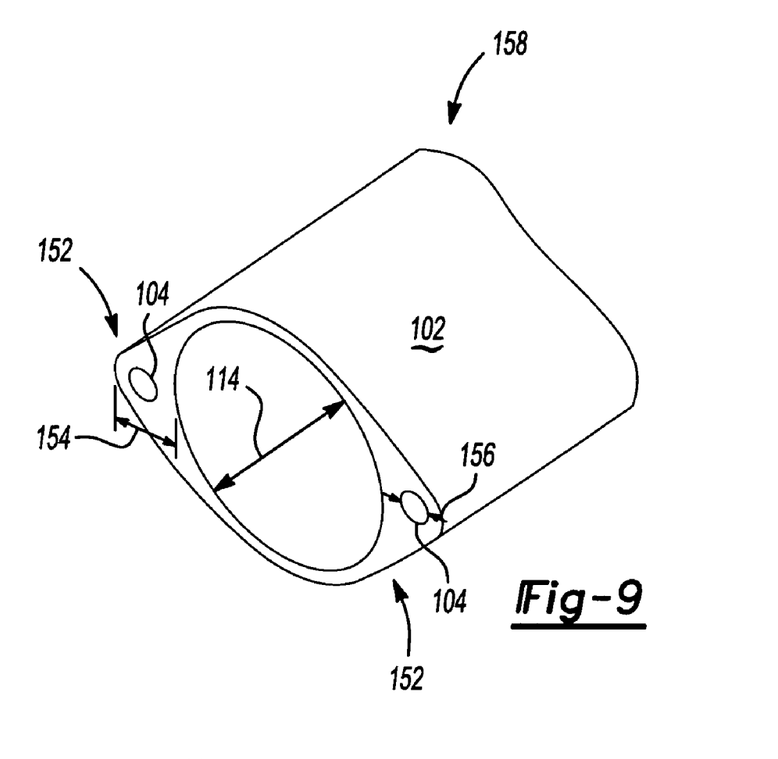
FIG. 9 is a partial perspective view showing the main cannula constructed in accordance with the various embodiments of the present invention showing the guide wire holding members contained within the walls of the main cannula.

The main cannula 102 also includes a wall thickness that is generally indicated by reference numeral 118. The wall thickness 118 of the main cannula 102 is generally the same throughout portions of the main cannula 102. Other embodiments of the present invention, however, may vary the wall thickness 118 of the main cannula 102 by, for example, using different configurations of an exterior of the main cannula 102, an example of which is shown in FIG. 9.

Figure 5:
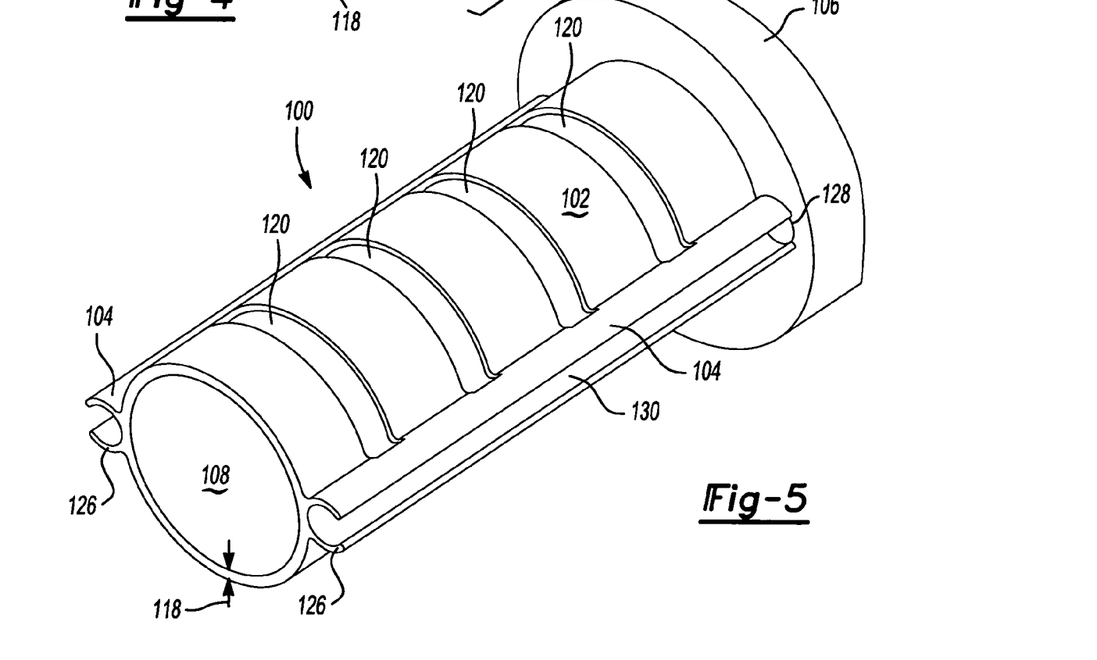
FIG. 5 is similar to FIG. 2 but shows the cannula member having graduated ring portions formed thereon.

With reference to FIG. 5, the medical device 100 may be configured with a plurality of graduated ring portions 120. The graduated ring portions 120 cover at least partially the exterior of the main cannula 102. It will be appreciated that the graduated ring portions 120 can be configured as indentations along the exterior of the main cannula 102 such that the wall thickness 118 at each of the graduated rings 120 is less than an adjacent portion of the exterior of the main cannula 102 is not contained in the graduated ring 120. It will additionally be appreciated that the graduated ring portions 120 can be configured such that the wall thickness 118 at each of the graduated rings 120 is greater than the adjacent portion of the exterior of the main cannula 102 not otherwise within one of the graduated rings 120. For example, a user (not shown) could run their hand across the exterior of the main cannula 102 and either feel indentations where the wall thickness 118 was less than—or feel raised bumps where the wall thickness 118 was greater than—the adjacent exterior of the main cannula 102 not otherwise having a graduated ring 120.

With reference to FIG. 12, it will be appreciated that the graduated rings 120 can be configured to hold the medical device 100 in the incision 110. More specifically, as the medical device 100 is inserted into the incision 110 the graduated ring portions 120 will grab and/or hold the incision 110 more securely thus making it more difficult to remove the medical device 100 from the patient.

Figures 6, 7:
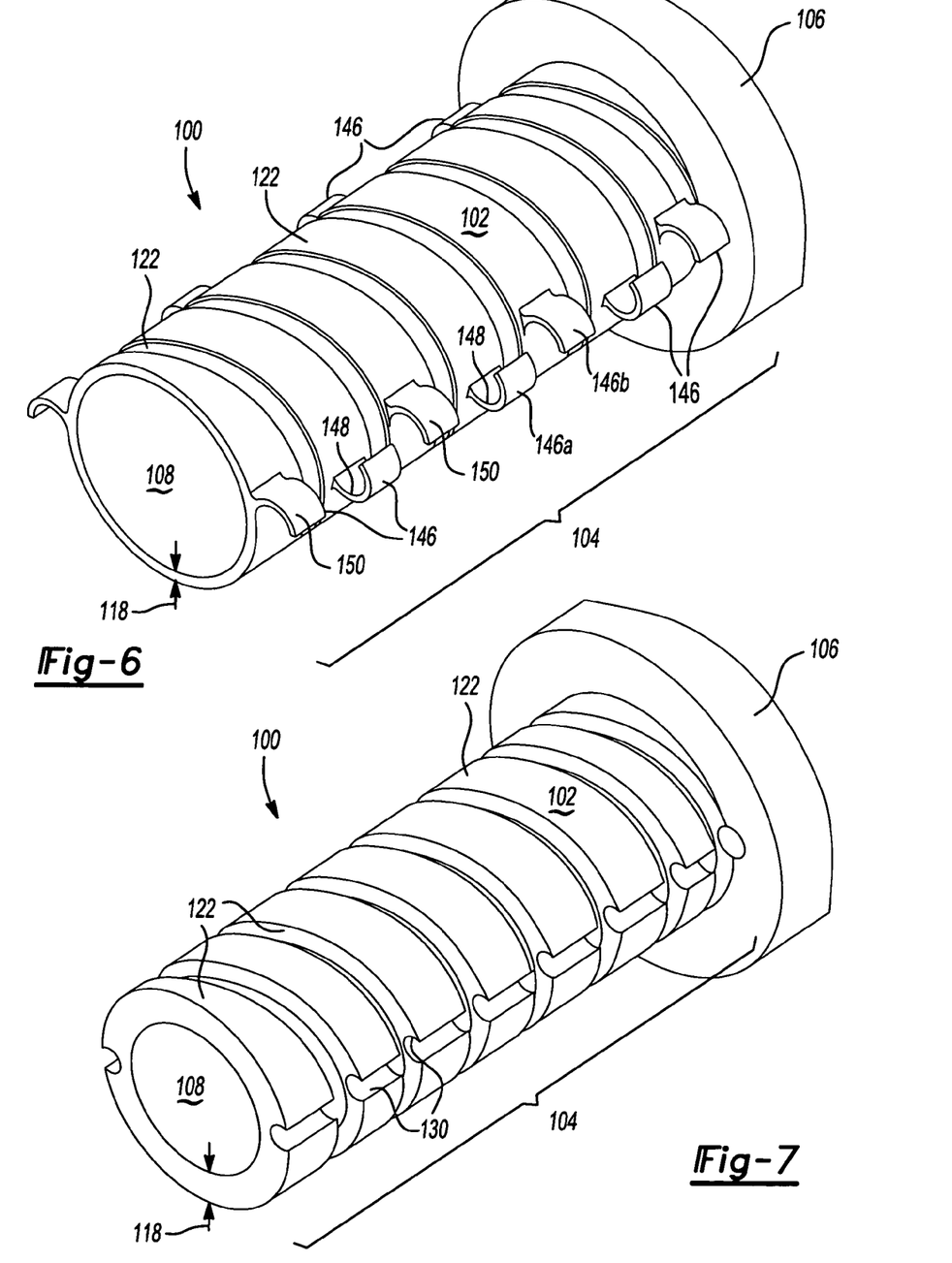
FIG. 6 is similar to FIG. 4 but shows the cannula member having threaded portions formed thereon and the guide wire holding members configured as the plurality of the curled portions.
FIG. 7 is similar to FIG. 5 but shows the cannula member having the threaded portions and the guide wire holding members formed therein.

As shown in FIGS. 6 and 7, the exterior of the main cannula 102 can be configured to include threaded portions 122 over at least a portion of the exterior of the main cannula 102. The threaded portions 122 are configured to, among other things, assist in inserting the medical device 100 through the incision 110, (FIG. 13) and into the patient. The threaded portions 122 can be configured to grab the incision 110 as the medical device 100 is rotated into the patient (not shown). Moreover, the medical device 100 can be inserted into the patient and the threaded portions 122 can be configured so that depth adjustments can be easily obtained by simply rotating the medical device 100. Similar to the graduated ring portions 120, as shown in FIG. 5, the threaded portions 122 can be configured with raised portions or recessed portions having a larger wall thickness 118 or a smaller wall thickness 118 compared to the adjacent non-threaded portions 122 of the exterior of the main cannula 102 respectively. Furthermore, the medical device 100 can be configured with differing wall thickness 118 such that certain configurations of the guide wire holding members 104 may facilitate differing wall thicknesses 118.

With reference to the various Figures the guide wire holding member 104 can be configured to hold a guide wire 124. The guide wire holding member 104 can also be configured to hold fixation pins or steerable guide wires. It will be appreciated that guide wires and/or fixation pins may be inserted into and held by the guide wire holding members 104. It will be further appreciated that the guide wires can be flexible, partially rigid or completely rigid. The guide wires can also be steerable by mechanical linkage or by application of an electrical current, such as in the application of shape memory alloys like Nitinol. The thickness of the guide wires can also vary from a thin reliable wire to a rigid pin or rod. Nevertheless, the guide wire holding member 104 when connected with the guide wire 124, provides greater stability and greater control of the medical device 100 when inserted into the patient (not shown).

With specific reference to FIG. 3, the guide wire holding members 104 can also facilitate steering of the medical device 100. More specifically, the guide wires 124 can be steerable with various systems such as Nitinol wires that will change shape, thus change direction, in response to an electrical current. The guide wires 124 can also be directed with other external devices, such as a mechanical linkage, which can force the tip of the guide wire 124 to move in response to a signal and/or a force applied by various external controls. The medical device 100, therefore, can be constructed of a material, such as, but not limited to, latex or other flexible medical plastics which will bend and flex in response to the controllable motion of the guide wire 124. As the guide wire 124 changes direction and otherwise navigates within the incision 110 (FIG. 11), the medical device 100 can bend and move with the guide wires 124.

Figure 4:
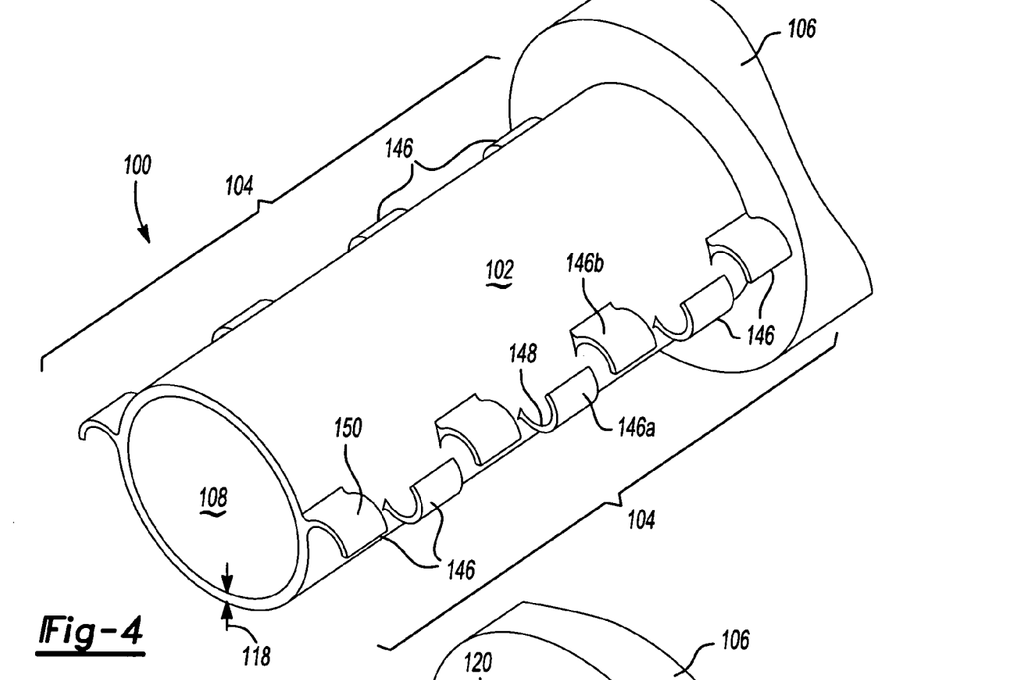
FIG. 4 is similar to FIG. 2 but shows the guide wire holding members configured as a plurality of curled portions.

As shown in various figures, a pair of guide wire holding members 104 is connected to the main cannula 102. It will be appreciated, however, a plurality of guide wire holding members 104 may be connected to the main cannula 102 such that three or more guide wire holding members 104 may be utilized. It will also be appreciated that one or more of the guide wires 124 can be inserted through one or more of the guide wire holding members 104. It will be appreciated that each of the guide wire holding members 104 may be identical or vary from one another. More specifically, the guide wire holding members 104 as depicted in FIG. 2, can be used in conjunction with the guide wire holding members 104 as depicted in FIG. 4 on the medical device 100. It will further be appreciated, therefore, while a single guide wire holding member 104 may be discussed hitherto and throughout, one or more guide wire holding members 104 may be connected to the main cannula 102 as needed such that discussion of a single guide wire holding member 104 does not limit the present invention as such.

Figure 8:
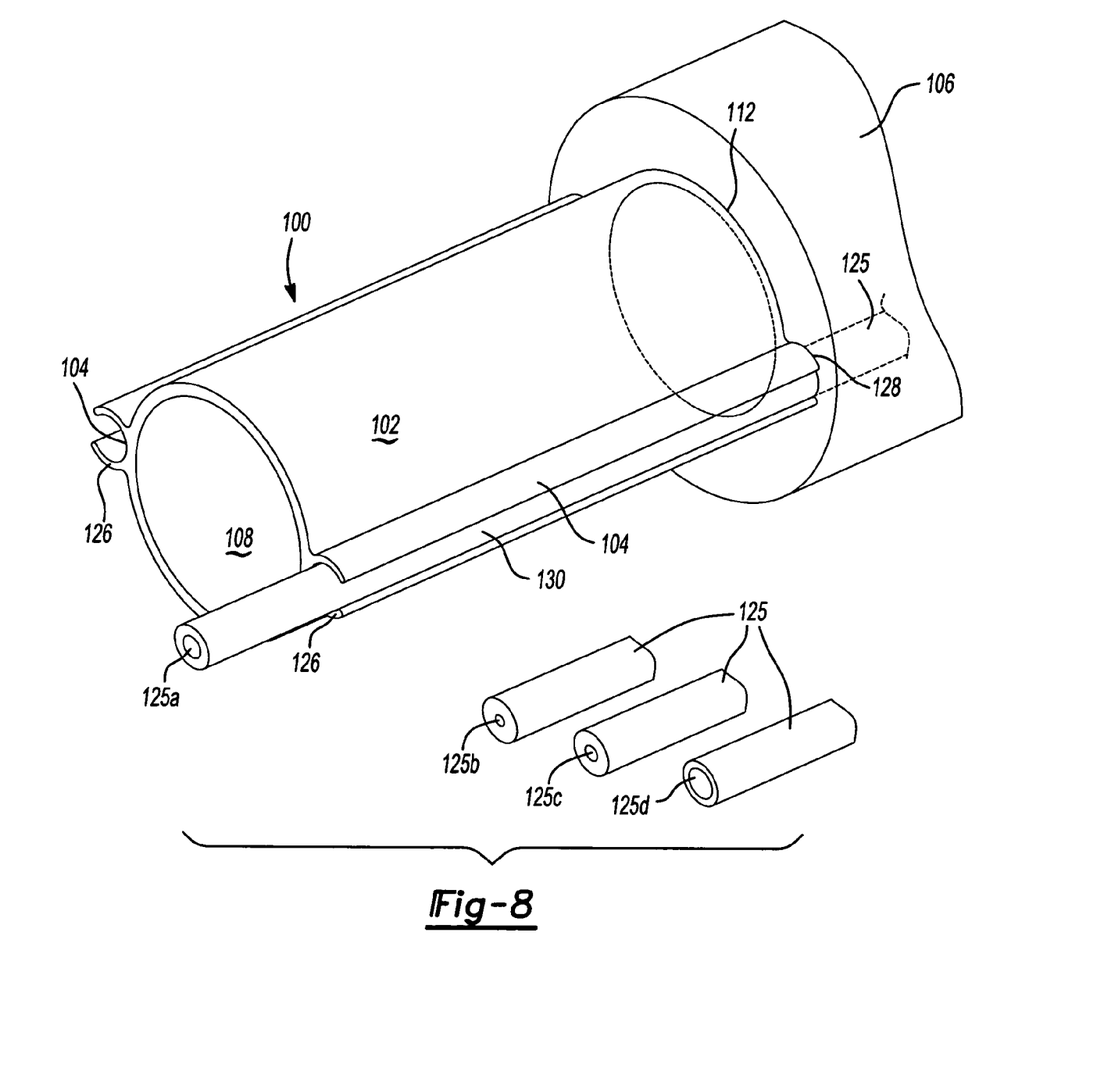
FIG. 8 is similar to FIG. 2 but shows inserts with variable inside diameters disposed within the guide wire holding members.

With reference to FIG. 2 and FIG. 5, the guide wire holding member 104 is configured as a continuous c-shaped channel. With reference to FIG. 7, the guide wire holding member is configured with c-shaped channel interrupted with the threads 122. In FIG. 8, the guide wire holding member 104 includes an insert 125 disposed therein. The insert 125 includes varying inner diameters 125A, 125B, 125C and 125D. The guide wire 124 of varying configurations can be inserted into the insert 125. As such, the guide wire holding member 124 need not be configured to accommodate varying configurations of the guide wire 124 but only the insert 125. The insert 125, in contrast, can have fixed outer diameter while having a variable inside diameter thus providing modular functionality to accommodate various configurations or diameters of the guide wire 124.

The guide wire holding member 104 has a tip 126 on the same end as the main cannula tip 108. The guide wire holding member 104 has a guide wire holding member connecting point 128 which is distal from the guide wire holding member tip 126. As such, the guide wire holding member connection point 128 is open to the accessory portion 106 such that the guide wire 124 can be passed therethrough. The c-shaped channel of the guide wire holding member 104 can be configured as a generally circular channel such that walls 130 of the channel have about 270 degrees of material. It will be appreciated that if the walls 130 had 360 degrees of material the guide wire holding member would be configured similar to one of the pair of smaller tubes 14 as shown in FIG. 1. More specifically, the walls 130 of the guide wire holding member 104 include a first channel portion 132 and a second channel portion 134 connected to a base portion 136, all of which are connected to the main cannula 102, as shown in FIG. 10 in greater detail.

Figure 15:
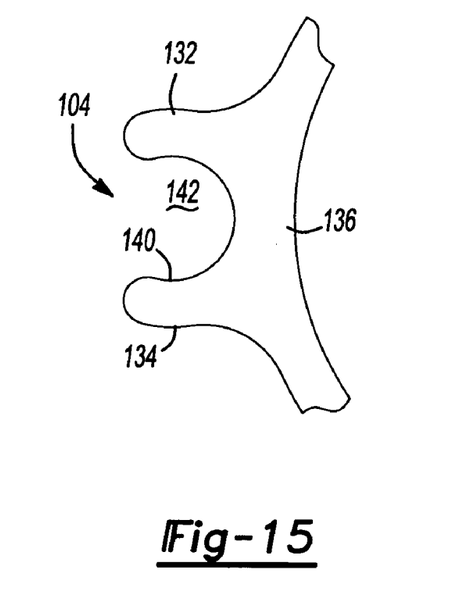
FIG. 15 is a partial front view of the guide wire holding member of FIG. 10 configured as a half circle.
Figure 16:
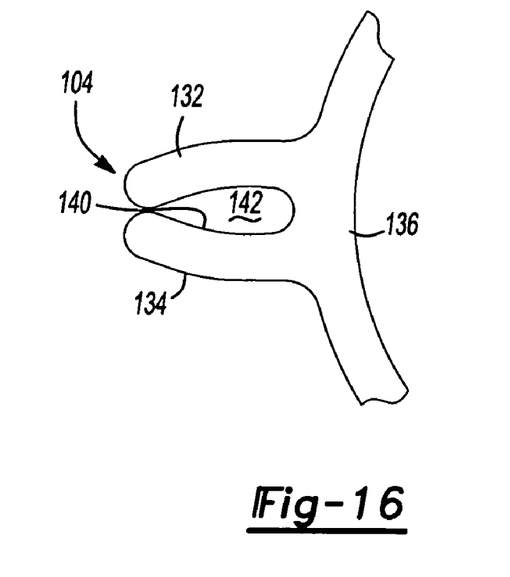
FIG. 16 is a partial front view of the guide wire holding member of FIG. 10 configured in a shape similar to a clam shell.
Figure 17:
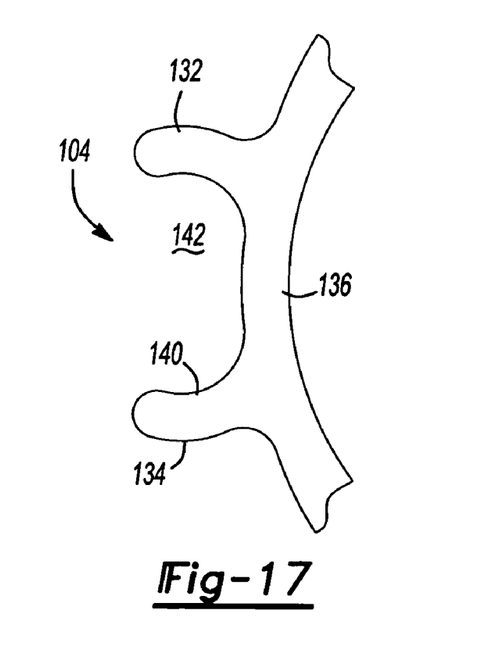
FIG. 17 is a partial front view of the guide wire holding member of FIG. 10 configured as an elongated oval shape.

In the various embodiments, the guide wire holding member 104 can be configured such that it forms an incomplete circle. For example, the material can be configured to occupy about 270 degrees. To that end, the first channel portion 132 and the second channel portion 134 can be symmetrical such that their respective arc lengths occupy about 135 degrees each. With reference to FIGS. 14, 15, 16 and 17, the arc length of the first channel portion 132 and the second channel portion 134 can also be asymmetrical. Moreover, the first channel portion 132 and the second channel portion 134 need not be continuous throughout the length of the main cannula 102 from the main cannula tip 108 to the main cannula connecting point 112. More specifically, the first channel portion 132, the second channel portion 134, and the base portion 136 from an interior concave portion 140 that defines an interior channel 142 throughout the guide wire holding member 104. In the various embodiments, the first channel portion 132 can be spaced from the second channel portion 134 such that the interior of the first channel portion 132 the base portion 136 and the second channel portion 134 neither form a perfect nor an incomplete circle but more of an elongated space capped by the two channel portions 132, 134; as shown in FIG. 17. Furthermore, the first channel portion 132 can be spaced from the second channel portion 134 a distance smaller than that would have formed the perfect or otherwise incomplete circle. More specifically, the first channel portion 132 and the second channel portion 134 are spaced close enough where the interior channel 142 may resemble a clamshell configuration rather than an imperfect circle, as shown in FIG. 16. Additionally, the interior channel 142 can be configured as almost a complete circle (FIG. 14) or as a half-circle (FIG. 15.)

Figure 10:
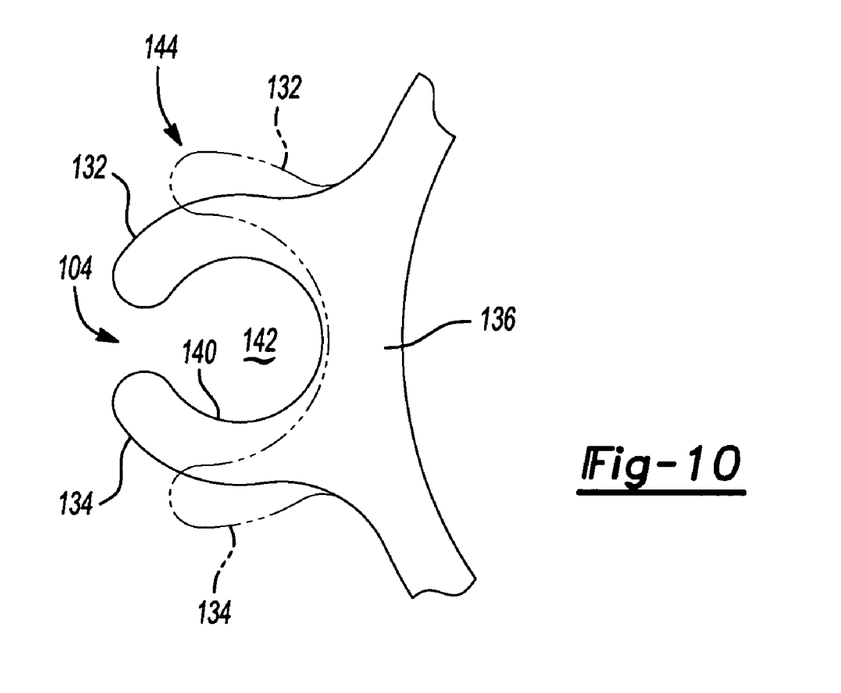
FIG. 10 is a partial front view of the guide wire holding member of FIG. 2 configured as a c-shaped channel and further showing (in shadow) the c-shaped channel in an expanded condition.

As shown in shadow in FIG. 10 the guide wire holding member 104 can be in a deflected position, generally indicated by reference numeral 144. More specifically, the guide wire holding member 104 can be constructed from a flexible material that allows the guide wire holding member 104 to be stretched. It will be appreciated that this stretching can occur when the medical device 100 is removed from the injection molding machine mold (not shown). Moreover, the guide wire holding member 104 may stretch into a deflected position 144 when the guide wire 124 is removed therefrom.

The guide wire holding members 104 are configured in a c-channel configuration to facilitate manufacturing and use of the medical device. While the guide wire holding members 104 may be configured as separate full length tubes, as shown in FIG. 1, this construction as noted above can be expensive and imprecise. As such the guide wire holding members 104 of the present invention are configured so that they can be more easily extracted from the injection mold and thus do not require the use of tapered pins with exacting alignment. By using the c-shaped guide wire holding member 104 as opposed to a long constant tube, the injection molding machine lay up mold can omit the use of the pins altogether, thus making the manufacture less costly and complex. Furthermore, the medical device 100 can be removed from the injection mold (not shown) by peeling it away or stretching it over portions of the mold as opposed to removing it from tapered pins as discussed above.

With reference to FIGS. 4 and 6, the guide wire holding member 104 is configured as a plurality of curled tabs 146. The plurality of the curled tabs 146 can be configured similar to the c-shaped channel as depicted in FIGS. 2, 5 and 7. More specifically, the curled tabs 146 can have a concave portion 148 and a convex portion 150. The plurality of the curled tabs 146 can be configured such that each of the curled tabs 146 is spaced axially along the main cannula 102 from each of the other curled tabs 146. Furthermore, each of the curled tabs 146 can be configured such that the concave portion 148 of a first curled tab 146a is facing a direction opposite from an adjacent curled tab 146b. It will be appreciated that the plurality of curled tabs 146 can be configured such that the concave portions 148 of each of the curled tabs 146 can be oriented such that the plurality of curled tabs 146 holds the guide wires 124 of various configurations.

It will be appreciated that in the various embodiments, the plurality of curled tabs 146 can be configured as about 135 degree arcs. It will also be appreciated that the arc length of material of each curled tab 146 can be less than or greater than 135 degrees of arc such that each curled tab 140 can have varying degrees of an arc length of material. It will be further appreciated that each individual curled tab 146 can otherwise be configured as generally orthogonal (not shown) from the exterior of the main cannula 102 such that each individual curled tab would not be curled but in such a relation to other tabs to secure the guide wire 124. The plurality of curled tabs 146 can also be configured to hold the guide wire 124 and not sandwich the guide wire 124 between each of the curled tabs 146. More specifically, each of the curled tabs 146 can be spaced from the adjacent curled tabs so that the guide wire 124 is held between the plurality of curled tabs 146 and not snuggly between them.

The plurality of curled tabs 146 are connected to at least a portion of the main cannula 102, but can otherwise occupy the complete length of the main cannula 102 from the main cannula tip 108 (FIG. 2) to the main cannula connecting portion 112 (FIG. 2). It will be appreciated that having curled tabs 146 along the entire length of the main cannula 102 is not required to provide suitable stability for the medical device 100 when inserted into the incision 110, as shown in FIG. 13.

With reference to FIG. 6, the exterior of the main cannula 102 is configured with threaded portions 122 throughout the length of the main cannula 102. It will be appreciated that the threaded portions 122 may intersect the guide wire holding members 104 in the spaces between the individual curled tabs 146. It will be further appreciated that the convex face 150 of the curled tabs 146 faces the direction that is required to turn and thus insert the medical device 100 into the incision 110 as shown in FIG. 10. In this situation, the concave face 148 of the curled tabs 146 faces the direction of rotation required to remove the medical device from the incision 110. Moreover, the concave portion 148 can face the direction of rotation required to extract the medical device 100, which can serve to further secure the medical device 100 in the incision 110.

The medical device 100 may be constructed of various materials suitable for use in a medial and/or a surgical arena. The medical device 100 may be formed of various metals such as but not limited to cobalt chrome or titanium which otherwise allows the user to sterilize the medical device 100 in a suitable sterilization process prior to use. Moreover, the medical device 100 may be constructed of a suitable sterile and disposable plastic that will be used for a single use and then discarded. If the medical device 100 is constructed of a single use plastic, the medical device 100 can be configured to be reduced in length as needed during the operation. More specifically, the medical device 100 can be extended or trimmed to size in situ and then inserted into the patient as needed.

The accessory portion 106 can be sized with a larger diameter as shown in the various figures. It will be appreciated, however, the accessory portion 106 is optional and can be removed altogether. Further, the accessory portion diameter can be the same or smaller than the main cannula diameter 116.

With reference to FIGS. 11, 12 and 13, the medical device 100 can be inserted into the patient by making the incision 110 in the patient and either thrusting or rotating the medical device 100 into the patient. The medical device 100 may be further stabilized by use of one or more guide wires 124 or fixation pins that are secured to the patient through the incision 110 and then connected to the medical device 100 to increase stability. The guide wire 124 may be inserted into the patient and secured in the incision 110 prior to the insertion of the medical device 100. It will be appreciated, however, the medical device 100 may be inserted into the incision 110 and the guide wire 124 subsequently can be inserted through the medical device 100 and subsequently secured to the incision 110. If the guide wires 124 are first inserted through the incision 110 and then secured to the patient, the medical device 100 is inserted into the incision 110 and connected to the guide wires 124 to increase stability. It will be appreciated that the medical device depicted in FIGS. 2 and 5 can be thrust into the incision 110 and later connected to the guide wires 124 or may be inserted over the guide wires 124 and then thrust into the incision 110. It follows that the medical device 100 depicted in FIGS. 6 and 7 may be thrust or rotated into the incision 110 and later secured to the guide wires 124.

With reference to FIG. 9, the main cannula 102 is shown with the guide wire holding members 104 connected thereto but disposed within an enlarged exterior wall of the main cannula 102 to create a smooth oval-shaped exterior contour generally indicated by reference numeral 152. It will be appreciated that a wall thickness 154 surrounding the guide wire holding members 104 is enlarged to accommodate a diameter 156 of the wire holding member. More specifically, the inner diameter (the tip diameter 114 through to the connecting point diameter 116) of the main cannula 102 remains constant, but the outer diameter is increased in asymmetrical fashion around the guide wire holding members 104 such that the exterior portion of the main cannula wraps around the guide wire holding members 104 to create the continuous oval-shaped exterior of the main cannula, as generally indicated by reference numeral 158. It will be appreciated that the threaded portions (FIG. 6) or the graduated rings (FIG. 5) may be incorporated into the exterior portions of the main cannula as shown in FIG. 6. It will also be appreciated that the wall thickness 154 need only be as thick to ensure the integrity of the walls between the guide wire holding members 104 and the main cannula 102. The wall thickness 154, therefore, may be twice the diameter of guide wire holding member 104. The wall thickness 154 may also be less or more thick depending on the material used for the main cannula 102 and the various configurations of the guide wire 124.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A medical device for placement in an incision and for use with a guide wire, the medical device comprising:
   a cannula member extending along a longitudinal axis, said cannula member having an outer oval-shaped exterior wall and defining an interior passage that extends along said longitudinal axis, where said internal passage and said exterior wall define a wall thickness therebetween;
   a first guide wire holding member formed within said wall thickness; and
   a second guide wire holding member formed within said wall thickness, substantially opposite said first guide wire holding member.

2. The medical device of claim 1 wherein said cannula member defines a smooth oval-shaped exterior contour.

3. The medical device of claim 1 wherein said cannula member is configured with threaded portions formed from said exterior wall.

4. The medical device of claim 3 wherein said threaded portions are recessed in said exterior wall.

5. The medical device of claim 3 wherein said threaded portions are raised relative to said exterior wall.

6. The medical device of claim 1 wherein said cannula member is configured with graduated ring portions formed from said exterior wall.

7. The medical device of claim 6 wherein said graduated ring portions are recessed in said exterior wall.

8. The medical device of claim 6 wherein said graduated ring portions are raised relative to said exterior wall.

* * * * *